United States Patent [19]

Khillan

[11] Patent Number: 5,449,620
[45] Date of Patent: Sep. 12, 1995

[54] APPARATUS AND METHOD FOR CULTURING EMBRYONIC STEM CELLS

[75] Inventor: Jaspal S. Khillan, Cherry Hill, N.J.

[73] Assignee: Thomas Jefferson University, Philadelphia, Pa.

[21] Appl. No.: 187,395

[22] Filed: Jan. 25, 1994

[51] Int. Cl.⁶ .......... C12M 3/00; C12M 1/22; C12M 3/04; C12N 5/26
[52] U.S. Cl. .................. 435/284; 435/240.2; 435/240.23; 435/285; 435/287; 435/297
[58] Field of Search .......... 435/240.2, 240.23, 284, 435/287, 297, 285, 301

[56] References Cited

U.S. PATENT DOCUMENTS

| | | | |
|---|---|---|---|
| 4,304,865 | 12/1981 | O'Brien et al. | 435/240.2 |
| 4,894,343 | 1/1990 | Tanaka et al. | 435/301 |
| 5,157,024 | 10/1992 | Gordon | 514/23 |

FOREIGN PATENT DOCUMENTS 2522014  8/1983  France.

OTHER PUBLICATIONS

Wood et al., Simple and efficient production of enbryonic stem cell-embryo chimeras by coculture, *Proc. Natl. Acad. Sci. USA* 1993, 90, 4582-4585.

Nagy et al., Derivation of completely cell culture-derived mice from early-passage embryonic stem cells, *Proc. Natl. Sci. USA* 1993, 90, 8424-8428.

Wood et al., Non-injection methods for the production of embryonic stem cell-embryo chimaeras, *Nature* 1993, 365, 87-89.

*Primary Examiner*—William H. Beisner
*Assistant Examiner*—Nancy J. Degen
*Attorney, Agent, or Firm*—Jane Massey Licata

[57] ABSTRACT

Apparatus and method for culturing at least two different cell types in close proximity are provided. A solid support having at least one depression wherein a controlled concentration of a selected cell type can be layered is employed in the invention.

5 Claims, 1 Drawing Sheet

APPARATUS AND METHOD FOR CULTURING EMBRYONIC STEM CELLS

This invention was made in the course of research supported by the National Institutes of Health. The Government may have certain rights in this invention.

BACKGROUND OF INVENTION

Gene targeting via homologous recombination in pluripotent embryonic stem (ES) cells to create chimeric animals is a powerful means of introducing specific mutations into the animal's genome. This technique also provides an opportunity to elucidate the function of genes.

The predominant method for the production of EScell-embryo chimeras has been the microinjection of a small number of ES cells into the blastocoel cavity followed by transfer of the developing embryo into pseudopregnant recipients for gestation. The target vector is introduced into ES cells by electropotation and the homologous recombinant clones are selected by treatment with G418 and gancyclovir. These cells are then injected into blastocysts to generate chimeric animals which are mated with the wild type animals to obtain germ line transmission of the mutation. While this method has been effectively used to produce chimeras, the cost of the necessary equipment and the length of time and level of skill required have posed practical limitations for this method.

Recently, alternative procedures to microinjection have been described based on the observation the ES cells readily aggregate with morulae. Therefore, chimeras can be produced simply by bringing the two cell populations into contact. Wood et al. (Proc. Natl. Acad. Sci. U.S.A. (1993) 90:4582-4585) described a procedure in which the embryo at the 4 to 8 cell stage or at the compact morula stage is cultured with the targeted ES cells. The ES cells are internalized into the developing blastocyst resulting in a high degree of chimerism in the animals born from these embryos. The chimeras are then cultured overnight to the blastocyte stage and transferred into pseudopregnant recipients for gestation.

A similar procedure was described by Nagy et al. (Proc. Natl. Acad. Sci. U.S.A. (1993) 90:8424-8428) involving the preparation of a "sandwich" consisting of a tetraploid embryo and a clump of ES cells.

The techniques described by Wood et al. and Nagy et al. involve culturing of embryos on a bed of ES cells to allow an unpredictable number of cells to attach to the embryo followed by the transferring of the embryo to another plate for culturing to the blastocyst stage. These aggregation methods, as compared to microinjection, require neither expensive equipment nor as high a level of expertise. However, these procedures also have limitations. First, the cells which adhere to the embryo also adhere to each other and to the pipette, and the denuded embryos also attach to each other as well as the pipette, thus causing damage to the embryo during transfer. Second, the transfer step sometimes leads to the dissociation of cells from the embryo resulting in the failure to obtain chimeric animals and damage to the embryo. Third, the number of cells attached to embryo cannot be controlled. Fourth, the contact between the cells and embryo is not very effective. In addition, the method described by Nagy et al. (1993) requires specialized skill in the preparation of the sandwich between the tetraploid embryo and the cell clumps. The number of cells in the clumps is difficult to control. Therefore, the developing embryo may be completely derived from the ES cells resulting in poor viability of the animals. A new apparatus and method of using this apparatus have now been developed which overcome the limitations of the discussed aggregation methods. The apparatus and method provide for: 1) minimal handling of denuded embryos which results in high rate of blastulation; 2) effective control of the number of cells to be incorporated into the embryos; 3) monitoring of incorporation of ES cells into the embryos; and 4) no opportunity for embryos to adhere to each other. In addition, no special skills are required to use the apparatus and only one step of co-culture is involved.

SUMMARY OF THE INVENTION

In one aspect, the present invention provides an apparatus for culturing at least two different types of cells in close proximity comprising a solid support having at least one depression wherein a controlled concentration of a selected cell-type can be layered into the depression.

In another aspect, the present invention provides a method for producing chimeric animals having specific targeted mutations in their genome through use of this apparatus.

BRIEF DESCRIPTION OF FIGURES

FIG. 1b is a greatly enlarged cross-sectional view taken along line 1b–1b of FIG. 1a.

DETAILED DESCRIPTION OF THE INVENTION

This invention relates to apparatus and methods of using apparatus designed to provide an efficient and cost-effective procedure for culturing at least two different types of cells.

Figure 1A:
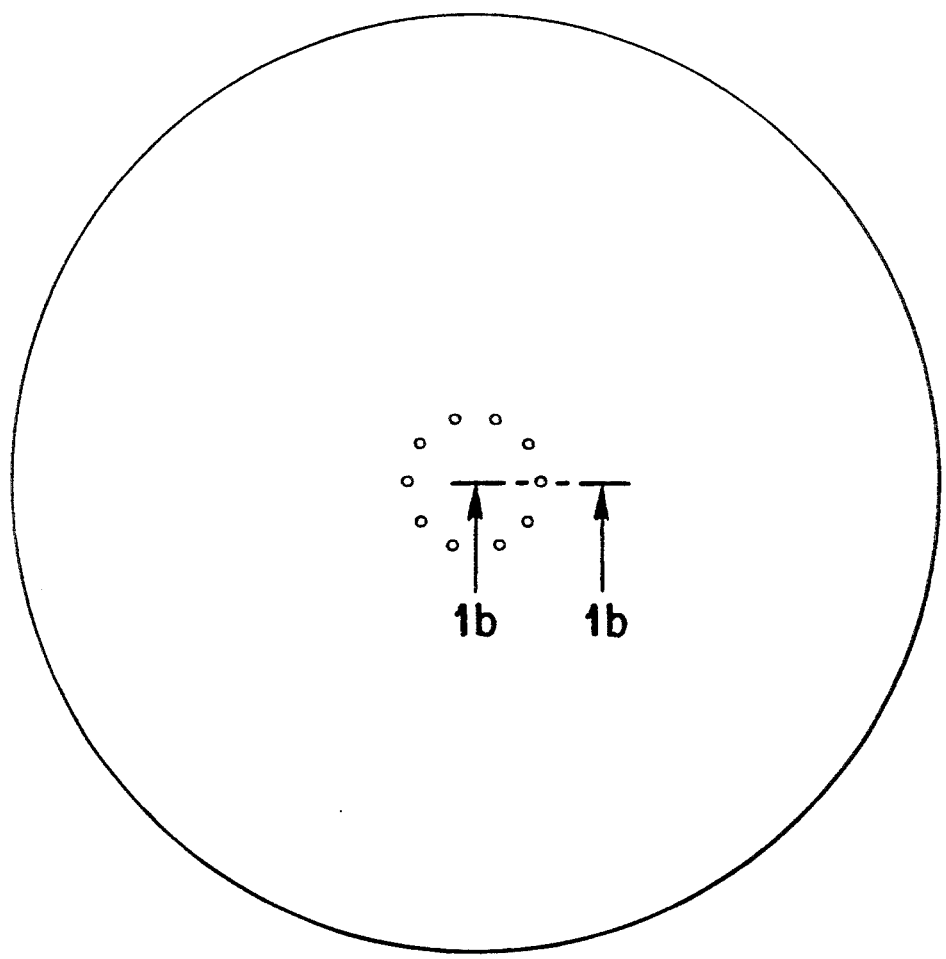
FIG. 1a shows a top view of one embodiment of the apparatus of the present invention. The figure depicts a 35 mm plastic petri dish which has been modified by drilling ten tapering depressions, most preferably 0.2–0.3 mm diameter at the top and 0.1–0.2 mm at the bottom in a circle of 0.5 cm. diameter at the center of the bottom of the dish.
Figure 1B:
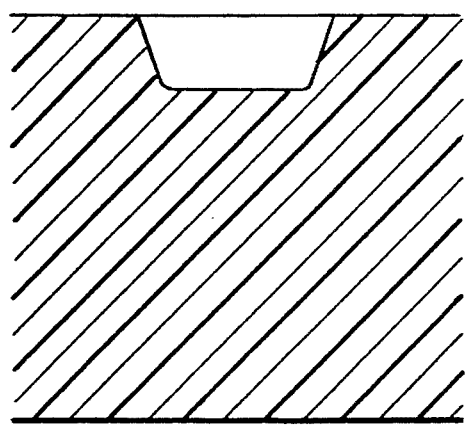

The apparatus provided in the present invention comprises a solid support, preferably plastic, more preferably a plastic petri dish, slide, or plate, having at least one depression wherein a controlled concentration of a selected cell-type can be layered into each depression. It is preferred that the plastic support has multiple depressions, most preferably ten, of about 0.2–0.3 mm in diameter at the top and 0.1–0.2 mm at the bottom, in a preferred embodiment. These depressions can be created by methods well known in the art. One embodiment of the invention is depicted in FIG. 1a and 1b.

This apparatus is useful in a number of applications wherein a close proximity of two or more different cell types is required. Examples of such applications include, but are not limited to, creation of gene targeted animals, embryo aggregation, cloning of embryos, cell hybrids and co-cultures. In the preferred embodiment, this apparatus provides a cost-effective alternate procedure to microinjection of embryonic stem cells into the blastocoel cavity and a more efficient procedure than the aggregation methods taught by Wood et al. and Nagy et al. for the production of chimeric animals with high reproducibility and minimal handling of embryos.

ES cells are cultured according to methods well known in the art. A selected concentration of ES cells is then layered into each depression of the apparatus of the present invention. Thus, the number of cells in each depression is controlled. In addition, the size and shape of the depressions provides for effective contact between the ES cells and the embryo. In a preferred embodiment, 8 to 10 ES cells are placed in each depression. The ES cells are allowed to settle for several minutes. A denuded morula or 8-16 cell embryo obtained from a pregnant animal by methods well known in the art is placed in each depression of the apparatus. The embryos are allowed to settle over the ES cells for several minutes at room temperature after which the apparatus is transferred to a $CO_2$ incubator for overnight culture. The ES cells will attach to the embryo during this time and contribute to the further development of the embryo to produce chimeric animals. No additional manipulation of the fragile embryo is required and the damage to the embryo is, therefore, minimized.

After overnight culture the embryos develop into blastocysts or compact morula. Each individual blastocyst is collected from the depressions of the apparatus, washed and transferred into foster mothers for gestation.

The method and apparatus of the present invention overcome the limitations for producing gene targeted animals using the microinjection and aggregation methods described by Wood et al. and Nagy et al. In addition, the method of this invention provides the following advantages over the previously described procedures.

The embryos are only handled once. Thus, damage to the embryos from multiple transfers is reduced or eliminated. Less damage results in higher rate of implantation. In addition, since each embryo is confined to a separate well in the present invention, there is no opportunity for embryos to adhere to each other.

The number of ES cells to be incorporated into embryos can also be effectively controlled resulting in improved reproducibility. In addition, the incorporation of these ES cells into the embryo can be monitored. The procedure of the instant invention involves only one step of co-culture which is a relatively simple process for those skilled in the art. No expensive equipment is required, only the apparatus comprising a solid support having at least one depression.

The following examples illustrate certain aspects of the present invention and are not intended to limit the same.

EXAMPLES

Example 1: Isolation of Embryos

Three to three and one-half week old female C57BL6 and CD1 inbred mice were superovulated with 5 IU of pregnant mare serum gonadotropin (PMSG) followed 48 hours later by Human chorionic gonadotropin (HCG) hormone. The females were mixed with the stud males. The following day the females with vaginal plugs were separated and sacrificed on day 2.5 with the day of plug as day 0. The compact morulas were isolated by flushing the uteri with Brinster's medium and the embryos were cultured and stored in this same medium.

Example 2: Embryonic Stem Cell Preparation

All the procedures for culture of ES cells were carried out according to procedures well-known in the art. The cells from J1 embryonic stem cell line were cultured in embryonic stem cell culture medium with 1,000 IU of Lymphocyte Inhibitory Factor (LIF) and were harvested by trypsinization. The cells were resuspended as a single cell suspension at the concentration of $2 \times 10^6$ cells/ml in ES medium.

Example 3: Removal of Zona Pellucida

Healthy and well compacted morulas or 8-16 cell embryos were incubated with acidified Tyrode's solution (137 mM NaCl, 2.7 mM KCl, 1.6 mM $CaCl_2 2H_2O$, 0.5 mM $MgCl_2 6H_2O$, 5.6 mM glucose and 0.4% polyvinylpyrrolidone pH 4.0). After the dissolution of zona the embryos were washed in excess volume of Brinster's medium avoiding sticking of embryos to each other and transferred to a drop of Brinster's medium under paraffin oil.

Example 4: Culture of ES Cells with Embryos

To provide a better contact with the embryos and to control the number of cells associating with the embryo, a specialized apparatus was designed for the purpose. On the bottom of a 35 mm petri dish about ten depressions or microwells of 0.2-0.3 mm diameter were drilled in a circle of 0.5 cm. diameter. The ES cells were diluted at the desired concentration with the Brinster's medium. Thirty $\mu l$ of the cell suspension was layered over the microwells and covered with paraffin oil. The cells are allowed to settle for about 15 minutes in a $CO_2$ incubator. The zona free embryos were collected from the incubation chamber and transferred to the microwells containing the ES cells. One embryo was placed in each microwell. The embryos were allowed to settle over the cells for about 10 minutes at room temperature after which the petri dish was transferred to a $CO_2$ incubator for overnight culture.

Example 5: Scoring of the Embryos

After overnight culture the embryos were monitored for the integration of cells. The embryos were monitored visually under a dissecting microscope at 60 X magnification. The integration was considered successful if the embryo developed into a morula or well expanded blastocyst and no ES cells were seen. Data from four different culture experiments is shown in the following table.

| Experiment Number | Number of Embryos | Overnight Culture | Percent |
|---|---|---|---|
| 1 | 8 | 8(2) | 100 |
| 2 | 40 | 36(18) | 90 |
| 3 | 53 | 50(20) | 94 |
| 4 | 26 | 24(9) | 90 |

More than 90% of the morulas developed into blastocysts. Similarly about the same number of 8-16 cell embryos developed into compact morula after overnight culture. In both cases no separate ES cells could be seen indicating the integration of cells into the embryos. Almost all the compact morulas developed into blastocysts.

Example 6: Implantation of Blastocysts into Pseudopregnant Females

After overnight culture the expanded blastocysts were washed in excess volume of Brinster's medium and transferred into the uteri of 2.5 day pseudopregnant female mice. About 8–10 embryos were transferred into one of the uterine horns. The pups were either allowed to deliver naturally or delivered by cesarian section after 17 days of implantation. Newborn pups were screened by polymerase chain reaction (PCR) using primers specific for the targeting vector and were scored for chimerism after 7–8 days of birth on the basis of coat color by visual inspection.

Example 7: Germline Transmission

The chimeric animals are mated with the wild type C57BL animals to check for germline transmission and the progeny analyzed shortly after birth by PCR.

What is claimed is:

1. An apparatus for co-culturing embryos with embryonic stem cells comprising a solid support having at least one tapering depression, said tapering depression being about 0.2–0.3 mm in diameter at the top and 0.1–0.2 mm at the bottom wherein a controlled concentration of a selected cell-type can be layered into the tapering depression.

2. The apparatus of claim 1 wherein the solid support is plastic.

3. The apparatus of claim 2 wherein the solid support is a plastic petri dish.

4. The apparatus of claim 3 wherein the plastic petri dish has multiple depressions.

5. The apparatus of claim 4 wherein the petri dish has ten depressions.

* * * * *